(12) United States Patent
Pernu (10) Patent No.: US 12,239,446 B2
(45) Date of Patent: Mar. 4, 2025

(54) FEMALE SNAP CONNECTOR AS WELL AS ASSOCIATED DEVICES AND METHODS

(71) Applicant: Suunto Oy, Vantaa (FI)

(72) Inventor: Kimmo Pernu, Vantaa (FI)

(73) Assignee: Suunto Oy, Vantaa (FI)

( * ) Notice: Subject to any disclaimer, the term of this patent is extended or adjusted under 35 U.S.C. 154(b) by 683 days.

(21) Appl. No.: 17/537,691

(22) Filed: Nov. 30, 2021

(65) Prior Publication Data

US 2022/0192571 A1 Jun. 23, 2022

(30) Foreign Application Priority Data

Dec. 22, 2020 (FI) ........................................ 20206359

(51) Int. Cl.
*A61B 5/274* (2021.01)
*A61B 5/024* (2006.01)
*A61B 5/256* (2021.01)
*A61B 5/265* (2021.01)
*A61B 5/268* (2021.01)

(52) U.S. Cl.
CPC .......... *A61B 5/274* (2021.01); *A61B 5/02438* (2013.01); *A61B 5/256* (2021.01); *A61B 5/265* (2021.01); *A61B 5/268* (2021.01); *A61B 2562/125* (2013.01)

(58) Field of Classification Search
CPC . A44B 17/00; A44B 17/0023; A44B 17/0076; A61B 5/02438; A61B 5/256; A61B 5/268; A61B 5/274; A61B 5/28; A61B 5/291; A61B 5/296; A61B 5/297; A61B 5/6802; A61B 5/6804; H01R 12/778; H01R 4/58; H01R 13/03; H01R 13/11; H01R 13/111; H01R 13/50; H01R 13/627
See application file for complete search history.

(56) References Cited

U.S. PATENT DOCUMENTS

| 3,551,963 | A |   | 1/1971  | Mosher, Jr. et al. |
|-----------|---|---|---------|--------------------|
| 3,973,099 | A |   | 8/1976  | Morris             |
| 3,995,644 | A |   | 12/1976 | Parsons            |
| 4,785,508 | A | * | 11/1988 | Takeda ............... A44B 17/0076 24/114.7 |

(Continued)

FOREIGN PATENT DOCUMENTS

| EP | 2301372 A1 | 3/2011 |
| EP | 2679107 A1 | 1/2014 |

(Continued)

OTHER PUBLICATIONS

US 9,865,941 B1, 01/2018, Oster et al. (withdrawn)

*Primary Examiner* — Eun Hwa Kim
(74) *Attorney, Agent, or Firm* — Laine IP Oy (57) ABSTRACT

According to an example aspect of the present invention, there is provided a female snap connector with a base and a cap which opposes the base and forms a depth for the snap connector. The female snap connector further includes a socket that is formed into the cap for receiving the stud of a co-operational male snap connector. The base material of the female snap connector is or comprises a conductive polymer. The socket is set to deform elastically for complying to the passage of the complementary shape of the stud within the socket during insertion and removal of the stud in the depth dimension of the female snap connector.

14 Claims, 7 Drawing Sheets

(56) References Cited

U.S. PATENT DOCUMENTS

| | | | |
|---|---|---|---|
| 5,232,383 A * | 8/1993 | Barnick | A61N 1/048 600/394 |
| 5,489,215 A | 2/1996 | Wright | |
| 2009/0113678 A1 | 5/2009 | Shimizu | |
| 2013/0072049 A1* | 3/2013 | Sato | H01R 4/58 439/378 |
| 2013/0131460 A1 | 5/2013 | Yuen | |
| 2013/0152347 A1* | 6/2013 | Hasegawa | A44B 17/0052 24/681 |
| 2014/0206210 A1 | 7/2014 | Ritner | |
| 2014/0371568 A1 | 12/2014 | Selby et al. | |
| 2015/0357741 A1 | 12/2015 | Nazzaro et al. | |
| 2016/0022165 A1 | 1/2016 | Sackellares et al. | |
| 2020/0008746 A1 | 1/2020 | Berg et al. | |

FOREIGN PATENT DOCUMENTS

| | | |
|---|---|---|
| FR | 360591 A | 4/1906 |
| JP | H0824010 A | 1/1996 |
| KR | 20180116917 A | 10/2018 |
| WO | WO2010056947 A1 | 5/2010 |
| WO | WO2015036288 A1 | 3/2015 |

* cited by examiner

FEMALE SNAP CONNECTOR AS WELL AS ASSOCIATED DEVICES AND METHODS

FIELD

The present invention relates generally to electro-mechanic assemblies. More particularly, embodiments of the present electrode unit are particularly well suited for receiving, holding and enabling an electrical connection with male ends of a telemetric device. Examples of the present electrode assemblies are integrated within a heart rate monitor belt or garment.

BACKGROUND

Currently, there are heart rate monitor belts which people can wear underneath their clothing in order to monitor their heart rate. Such belts are typically designed such that a telemetric transmitter is detachably connected to a belt having two electrodes which are in contact with the user's skin in the chest region of the user's torso. The electrodes identify an electric ECG pulse caused by the heart and then the detachable telemetric transmitter transmits data indicative of the user's heart beat with the use of wireless magnetic near field communication or a radio signal to a remote receiver provided with a display. In many instances the remote receiver is provided in the form of a wrist watch, wrist top computer or other similar display carried by a user, typically on the user's wrist.

Since various acceleration and magnetic sensors can be integrated in small and lightweight devices, the telemetric data to be transferred may, instead of or in addition to the heart rate, comprise a plurality of measured variable data, such as working frequency, pedaling rate and pedaling frequency, travel speed, etc. The data to be transferred may additionally comprise data required for the identification of the user and/or the transmitter device.

It is preferably to have a telemetric transmitter which is detachable from a heart rate monitor belt for several reasons. From a consumer point of view, a user is typically sweating while using a heart rate monitor belt and it is therefore advantageous to be able to separate the electronic telemetric transmitter from the belt so that the belt can be washed. From a manufacturing point of view, the process for manufacturing the belt is substantially different from that of manufacturing the transceiver and therefore it is beneficial to be able to manufacture the components separately. Additionally, it is beneficial for one telemetric transmitter to be interchangeable with a plurality of belts.

Conversely, standard medical electrodes are known which include an electrode substrate, which is placed against the user's skin through a conductive gel or glue, and a male snap connector extending from the substrate. Such electrodes are coupled to various devices that feature a corresponding female snap connector. Commercially available examples of such standard medical electrodes include 3M Red Dot and Ambu products.

There exist numerous challenges in the art to the development of a means of detachably connecting an electrode and an associated device through a snap connecting interface. The main issue is the integrity of the connection between the male stud and the snap. Any amount over movement of the male stud within the snap will create electrical noise which makes difficult to impossible to accurately measure parameters such as a user's heart rate. Additionally, as a user is typically involved in strenuous activity while utilizing the product, the connection needs to withstand, and support the telemetric transmitter during such activity. As the depth of the snap decreases, the forces required to ensure a reliably stable connection will significantly increase.

Still further, it has become clear that the contact between the snap and the electrode may deteriorate over time, due to wear, corrosion, contamination etc. An improved electro-mechanic assembly for such a snap connector is thus sought for.

SUMMARY OF THE INVENTION

The invention is defined by the features of the independent claims. Some specific embodiments are defined in the dependent claims.

According to a first aspect there is provided a female snap connector with a base and a cap which opposes the base and forms a depth for the snap connector. The female snap connector further includes a socket that is formed into the cap for receiving the stud of a co-operational male snap connector. The socket is set to deform elastically for complying to the passage of the complementary shape of the stud within the socket during insertion and removal of the stud in the depth dimension of the female snap connector.

According to a second aspect there is provided an electrode unit having a body which mechanically connects an electrode to such a female snap connector. A conductive passageway is formed to the body for electrically connecting the electrode to the female snap connector.

According to a third aspect there is provided a telemetric device with an enclosure and a circuit board contained in the enclosure. The telemetric device further includes such a female snap connector mechanically and electrically connected to the circuit board and extending through the enclosure.

According to a fourth aspect there is provided a wearable device having a host garment to be worn by a user and two such electrode units incorporated to the host garment and positioned such that the female snap connectors are set adjacent to each other so as to receive cooperative male snap connectors of an associated telemetric device.

According to a fifth aspect there is provided a method for manufacturing such a female snap connector by producing the base and cap with an additive manufacturing method into an integral component.

According to a sixth aspect there is provided a method for manufacturing such an electrode unit by providing the electrode and the body, producing the female snap connector with the method according to the fifth aspect, and by providing the conductive passageway between the female snap connector and the electrode by bonding the body, the female snap connector, and electrode together as an integral component, wherein the conductive passageway is formed at least partly by the body having an electrically conductive base material connecting the snap connector to the electrode or by the body having an electrically conductive layer for connecting the snap connector to the electrode.

Various embodiments of the invention may comprise one or more features from the following list:
- the base and cap are formed as an integral component;
- the conductive polymer is a conductive elastomer;
- the matrix of the conductive elastomer is selected from a list comprising:
  - natural rubber,
  - thermoplastic polyurethane (TPU),
  - thermoplastic elastomer (TPE),
  - silicone, particularly polydimethylsiloxane (PDMS), EPDM rubber, and
styrene-butadiene rubber (SBR);
the material of the conductive particles is selected from a list comprising:
carbon;
poly(3,4-ethylenedioxythiophene) polystyrene sulfonate (PEDOT:PSS);
silver;
metals;
carbon black,
graphite,
graphene,
carbon nano particles,
polyacetylene (PA),
polyaniline (PANT),
polypyrrole (PPY),
poly(3,4-ethylenedioxythiophene):poly(styrene sulfonic acid) (PEDOT:PSS), nanoparticles of silver, gold, copper, nickel, and
alloys of any of the above;
the cap is divided into several parts by one or more gap(s) between the parts for increasing the elasticity of the cap;
the female snap connector comprises an external side for interaction with the male snap connector and an internal side opposing the external side;
the socket comprises a relieved, such as bevelled, entrance surface provided to the cap on the external side;
the socket comprises a pinch connected to the entrance surface;
the socket comprises an opening;
the narrowest part of the opening of the socket is defined by the pinch;
the socket comprises a rim on the internal side surrounding the opening or on the external side or both;
the female snap connector comprises a peripheral recess between the rim and the surrounding base for increasing the flexibility of the socket;
the enclosure comprises two cooperative enclosure parts;
the telemetric device comprises an electro-mechanical interface including one or more of said female snap connectors and a sealing member incorporating the one or more of said female snap connectors;
the sealing member seals the enclosure parts to each other;
the sealing member is configured to produce a watertight seal between the enclosure parts of the enclosure;
the bonding of the body, the female snap connector, and electrode involves casting, ultrasonic welding, heat heading, high frequency welding, gluing with conductive adhesive, or thermal bonding, and
the base and cap are formed of a conductive polymer material.

Considerable benefits are gained with aid of the present invention. Because the female snap connector is made from a base material which is or comprises a conductive polymer, there are fewer points of discontinuity in the electrical path between the snap connectors making the electrical connection very secure. On the other hand, the elasticity of the conductive polymer provides for a reliable mechanical connection as well.

Further benefits associated with certain embodiments will transpire here after.

BRIEF DESCRIPTION OF THE DRAWINGS

In the following certain exemplary embodiments are described in greater detail with reference to the accompanying drawings, in which.

EMBODIMENTS

Figure 1:
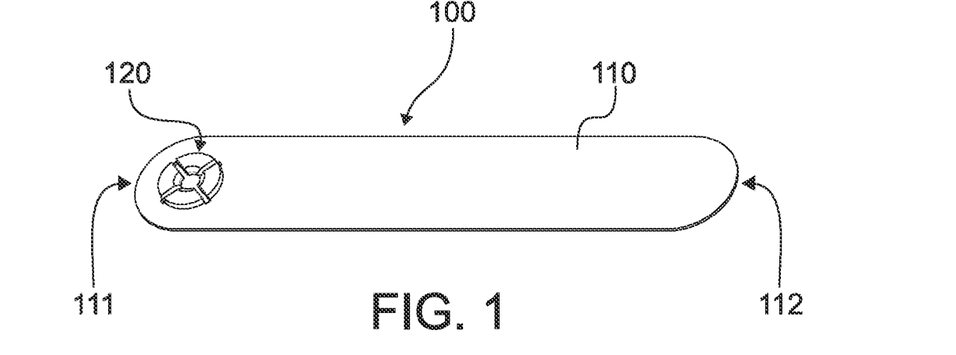
FIG. 1 illustrates a top perspective view of an electrode unit in accordance with at least some embodiments of the present invention.
Figure 2:
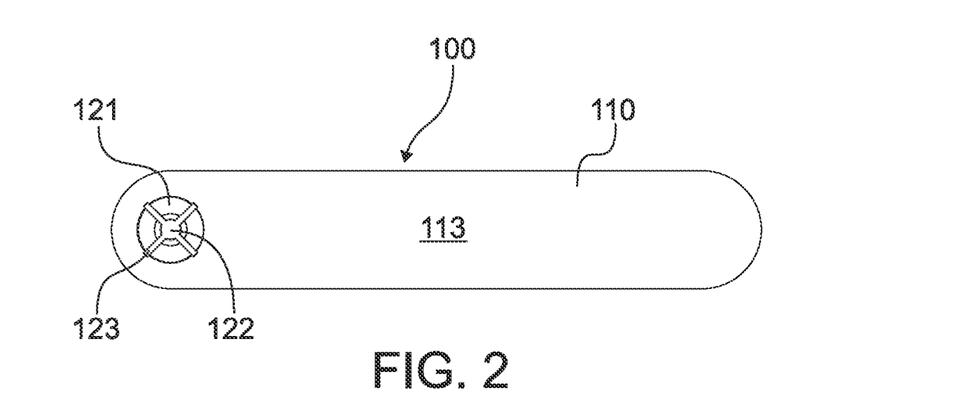
FIG. 2 illustrates a top elevation view of the electrode unit of FIG. 1.
Figure 3:
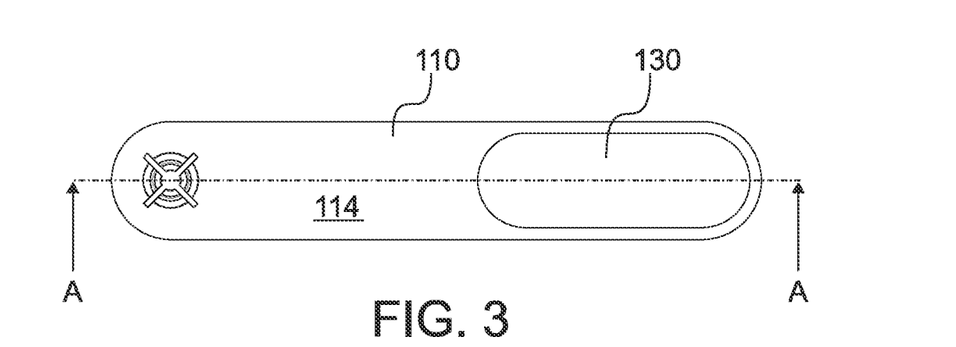
FIG. 3 illustrates a bottom elevation view of the electrode unit of FIG. 1.

FIGS. 1 to 3 show a general overview of an electrode unit 100 according to one embodiment of the present invention. The electrode unit 100 has three major sections; a female snap connector 120, an electrode 130, and a body 110 connecting the female snap connector 120 and the electrode 130 into an electrode unit 100. The electrode unit 100 is an elongated piece with a snap end 111 for housing the female snap connector 120 and an opposing electrode end 112 for housing the electrode 130. The body 110 may alternatively extend beyond the female snap connector 120 and 130, whereby the body 110 need not terminate to said ends 111, 112.

The electrode unit 100 is intended to be placed to a skin contact with the user. In particular, the electrode unit 100 may be integrated into a wearable device, such as a heart rate monitor belt or a piece of sporting apparel, which is worn around the user's torso so as to place the electrode 130 in appropriate locations to detect heart rate signals from the user's anatomy. For this purpose, the electrode unit 100 has an internal side 114 for facing the user and an external side 113 facing away from the user. Accordingly, the electrode 130 is provided on the internal side 114 of the body 110.

The female snap connector 120 is positioned such to interface with a telemetric device which is to be attached to the body 110 on the external side 113 thereof. In a typical application the electrodes of a heart rate monitor belt identify an electric ECG pulse caused by the heart and then the detachable telemetric device transmits data indicative of the user's heart beat with the use of wireless magnetic near field communication or a radio signal to a remote receiver provided with a display. In many instances the remote receiver is provided in the form of a wrist watch, wrist top computer or other similar display carried by a user, typically on the user's wrist.

Let us first consider the electrode 130. The electrode 130 is intended and configured to detect bio signals generated by the user, such as EKG, EMG, EEG, EOG, bio-impedance (BIO-Z), or electro-dermal activity (EDA) signals, and to convert those signals to be output to a telemetric device which is to be connected to the electrode 130 through the female snap connector 120. There are several suitable constructions for establishing such bio signals.

According to one embodiment the electrode 130 is provided with a piece of electrically conductive elastomer.

Examples of such elastomers include thermoplastic urethane and thermoplastic elastomer compounded with an electrically conductive material, such as carbon. Such conductive elastomer composites are known and available and often involve a polymer matrix, particularly a thermoplastic elastomer, mixed with carbon agglomerates before extrusion or other additive manufacturing stage. Alternative doping materials include poly(3,4-ethylenedioxythiophene) polystyrene sulfonate (PEDOT:PSS), silver, metals, carbon black, graphite, graphene, carbon nano particles, polyacetylene (PA), polyaniline (PANT), polypyrrole (PPY), poly(3, 4-ethylenedioxythiophene):poly(styrene sulfonic acid) (PEDOT:PSS), metals and their nanoparticles, such as silver, gold, copper, nickel, and alloys of metals. Alternative matrix materials include conductive polymer nanocomposites (CPNs) natural rubber, thermoplastic polyurethane (TPU), silicone, particularly polydimethylsiloxane (PDMS), EPDM rubber, and styrene-butadiene rubber (SBR). With the electrode produced from a singular material or composite having conductive properties, the electrode 130 may be constructed as a very durable and reliable component of the electrode unit 100 with only few or no points of discontinuities between the electrode 130 and the telemetric device.

According to another embodiment the electrode 130 is assembled from an electrically non-conductive substrate and an electrically conductive layer carried by the substrate. The substrate is preferably flexible to conform to the shape of the user's anatomy. Suitable substrate materials include conventional thermoplastic urethane films, silicone, EPDM, knitted, weaved or non-woven fabrics or any combination of the above. The electrically conductive layer may be provided with printing, laminating, or with other deposition methods. For example, the electrically conductive layer may be printed with a conductive ink, which are commercially available.

The body 110 is attached to or preferably formed as an integral part of the electrode 130. According to one embodiment the body 110 is injection molded as a chassis including openings for receiving the female snap connector 120 and the electrode 130. According to another embodiment the body 110 is produced simultaneously with the electrode 130 in a single stage additive manufacturing stage. The additive manufacturing stage may use one material for the electrode 130 and another for the body 110 or they may be produced from the same material. According to yet another embodiment the body 110 is produced by die-cutting from film or fabric sheets, for example. The material of the body 110 is preferably selected from soft and compliant materials to ensure a comfortable using experience for the user. Suitable materials include conventional thermoplastic urethane films, silicone, EPDM, knitted, weaved or non-woven fabrics or any combination of the above. The body 110 may be incorporated into an electrically insulating receiving structure, such as fabric or any foreseeable material so as to produce a garment, a wearable item, etc. A practical application would be to knit, glue, or otherwise attach the body 110 into a sports bra, wherein the fabric of the sports bra would cover the body 110 of the electrode unit 100.

Figure 4:
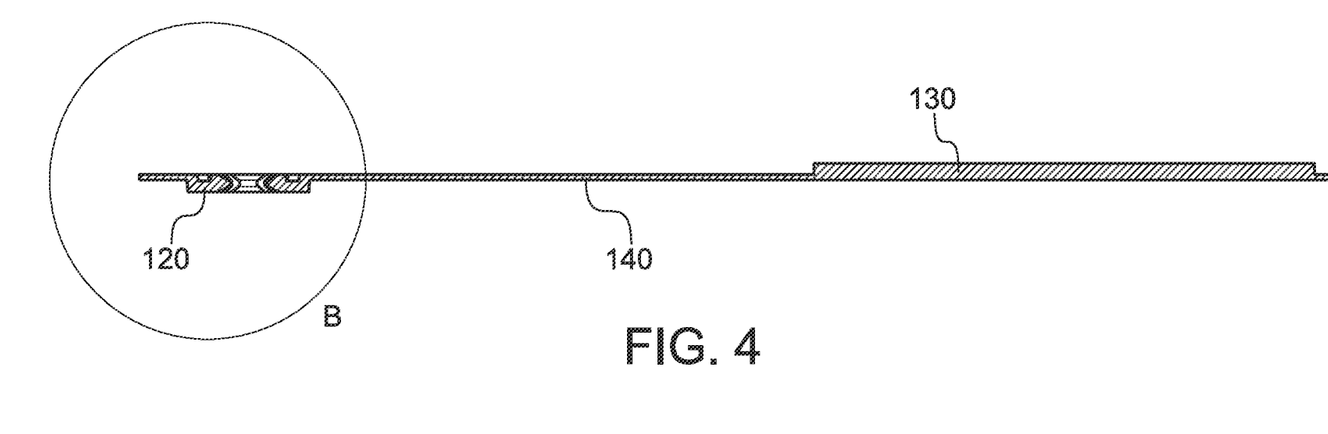
FIG. 4 illustrates a cross-sectional view of the electrode unit of FIG. 3 taken along line A-A.
Figure 5:
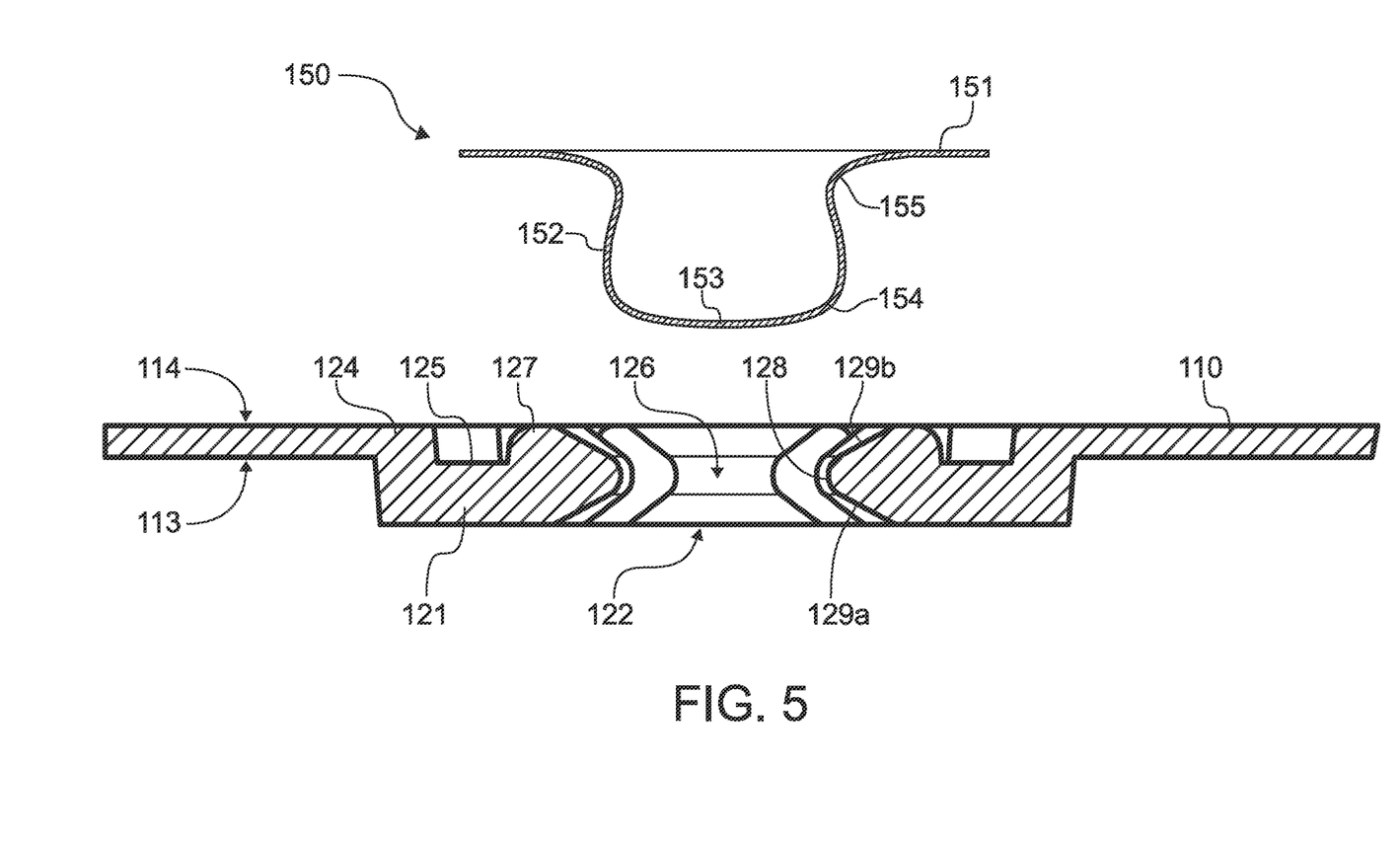
FIG. 5 illustrates a detail view of area B of FIG. 4 with a cooperative male snap connector in an approaching state.
Figure 6:
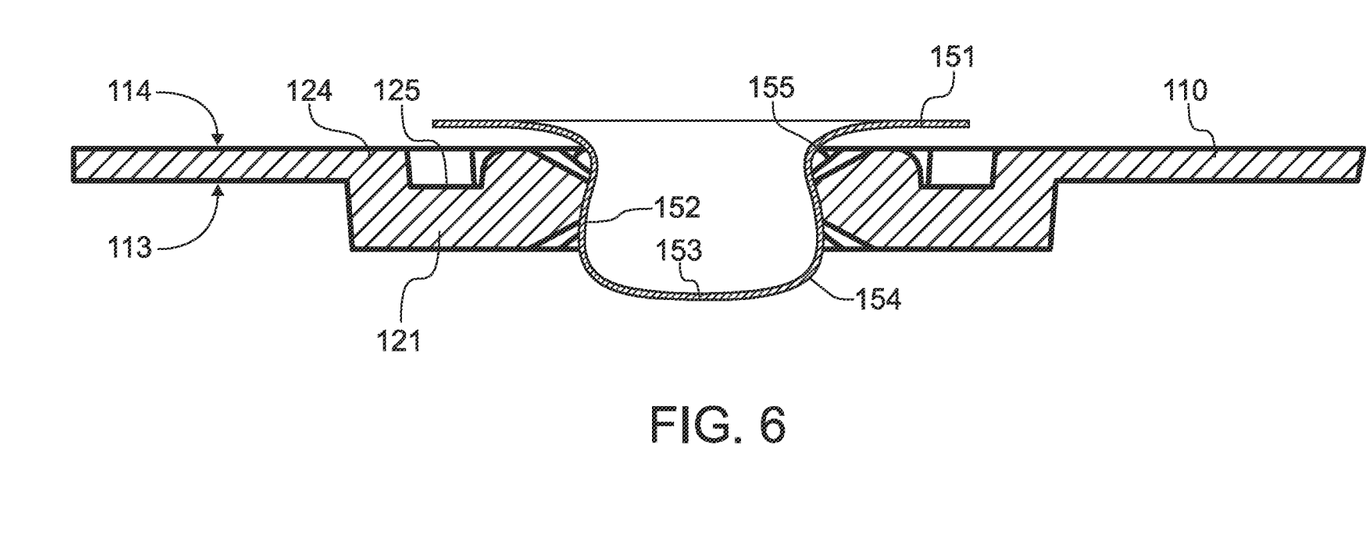
FIG. 6 illustrates the female and male snap connectors in a mutually connected state.

Turning now to the female snap connector 120 which is generally shown in FIGS. 1 to 4 and in detail in the enlarged cross-sectional views of FIGS. 5 and 6. The snap connector 120 protrudes from the body 110 to the external side 113. The orientation could alternatively be reversed, wherein the female snap connector would protrude from the body to the internal side (not shown in the FIGURES). The female snap connector 120 forms a generally cylindrical receptive recess in the electrode unit 100 for the corresponding stud of a male snap connector of the interfacing telemetric device. The generally cylindrical shape is shown only for exemplary illustrative purposes and it is to be understood that the general appearance could be varied. The female snap connector may, for example, exhibit a generally prismatic, trunco-conical, oval or any foreseeable shape.

As is shown in FIGS. 1 to 3, female snap connector 120 has a cap 121 protruding from the body 110 and including a socket 122 for the stud. The female snap connector 120 is constructed as a compliant member so as to elastically deform during the passage of the complementary shape of the stud within the socket 122, when the stud is inserted to or removed from the female snap connector 120. The elasticity is achieved on the one hand by constructing the female snap connector 120 from an elastomer. The elasticity is increased on the other hand with relieves made into the shape of the female snap connector 120. For example, the cap 121 may, as shown in FIG. 2, be divided into several parts, such as sectors, by gaps 123 provided between the parts for increasing the elasticity of the cap 121. The illustrated embodiment includes four radial gaps 123 dividing the cap 121 into quadrants. The number, placement, size, and/or shape or the gaps 123 may be varied. For example, a variant with one, two, three, or more than four is foreseen. It follows that a cap with two, three, or more than four parts, e.g. sectors, is foreseen. The purpose of the gap or gaps 123 is to facilitate the elastic opening of the socket 122 during insertion and removal of the corresponding male snap connector. This, in turn, will protect the female snap connector 120 from sustaining damage. On the other hand, such mechanical relief will enable adjustment of the force required to operate the connector in addition to or instead of optimizing the material. Again, it is to be understood that the cap 121 may have a shape different to the generally cylindrical shape shown in the FIGURES. Indeed, a generally prismatic or trunco-conical shape could, for example, be foreseen.

The female snap connector 120 has a base portion 124 which has a generally circular or otherwise closed peripheral shape through which the female snap connector 120 is connected or integrated to the surrounding body 110 of the electrode unit 100. The female snap connector 120 may be integrated to the body 110 by producing the female snap connector 120 and the body 110 in a single stage additive manufacturing process, such as injection molding. The injection molding may be performed single a single raw material or as a double component injection molding. Alternatively, the female snap connector 120 may be pre-fabricated and placed in the mold for molding the body 110 of the electrode unit 100. The female snap connector 120 itself is preferably injection molded.

FIG. 5 shows further shapes for increasing the compliancy of the socket 122 to the shape of an associated male snap connector 150 shown detached from the female snap connector 120 in FIG. 5. The socket 122 is designed to form a complementary shape to that of the stud of the male snap connector 150 of the telemetric device but also to comply to that shape during attachment and detachment of the telemetric device. During the attachment and detachment of the telemetric device the socket 122 is configured to undergo elastic deformation so as to comply to the passage of the complementary shape of the stud within the socket 122 during insertion and removal of the stud in the depth dimension of the female snap connector 120.

The cap 121 is connected to the base 123 through a connecting part defining the depth of the female snap connector 120. The cap 121 forms the socket 122 that has an opening 126 extending there through. The cap 121 transitions from the external side 113 to the internal side 114 through a relieved shape which envelops the socket 122. Viewing from the external side there is first a relieved entrance surface 129a. The entrance surface 129a may be bevelled, as illustrated, rounded, or otherwise relieved in respect to the surrounding cap 121 to lead the stud into the socket 122. The entrance surface 129a terminates to a pinch 128 which defines the narrowest part of the socket 122 and thus the diameter of the opening 126. The pinch 128 is intended to engage the side of the stud. The signal, which is detected by the electrode 130, is delivered to the telemetric device through the interface between the pinch 128 and the stud. To facilitate smooth movement of the stud, the pinch 128 is preferably rounded. The opening 126 is surrounded by a rim 127 on the internal side 114. The pinch 128 is connected to the rim 127 through another transitional surface, namely a rear surface 129b. The rear surface 129b is also preferably relieved, e.g. bevelled, in respect to the rim 127.

A peripheral recess 125 is provided to the female snap connector 120. The recess 125 may be provided, for example, between the rim 127 and the base 124 to further increase elasticity of the female snap connector 120. A peripheral recess 125 may be provided on either side or both sides of the female snap connector 120. An alternative or additional recess could be provided in the cap 121. The size and/or shape of the peripheral recess 125 may be varied. For example, a variant with more than one recess per side is foreseen. The purpose of the peripheral recess 125 is to facilitate the elastic opening of the socket 122 during insertion and removal of the corresponding male snap connector. This, in turn, will protect the female snap connector from sustaining damage. On the other hand, such mechanical relief will enable adjustment of the force required to operate the connector in addition to or instead of optimizing the material. It is particularly beneficial to combine the one or several peripheral recess(es) 125 to the one or several radial gap(s) 123 to optimize the resiliency of the female snap connector 120.

FIG. 6 shows the exemplary male snap connector 150 inserted into the receptive socket 122 of the female snap connector 120. The male snap connector 150 is shown to approach the female snap connector 120 from the external side 113. However, the male snap connector 150 could alternatively be inserted from the opposite side, i.e. from the internal side 114. In other words, the snap fit connector 120, 150 has a double-sided action. The male snap connector 150 is made of an electrically conductive material, such as steel or other metal. The stud can be constructed by shaping sheet metal into the desired shape or machined from a block of raw material, for example. The male snap connector 150 therefore preferably maintains its shape during use. The male snap connector 150 features a generally flat annular flange 151 and a stud which extends from the flange 151. The stud is formed by a generally cylindrical side 152 which terminates to a bottom 153. To facilitate smooth insertion to and retraction from the female snap connector 120, the flange 151, side 152, and bottom 153 are connected to each other through rounded transitions 154, 155 giving the stud 153-155 a rounded general appearance. More specifically, the transition 155 between the side 152 and the flange 151 reduces the diameter of the profile of the stud compared to the largest diameter of the side 152, whereby a counterdraft shape is created. The counterdraft shape prevents, in part, the stud from slipping out of the socket 122 of the female snap connector 120.

When the female and male snap connectors 120, 150 are connected to each other the pinch 128 of the female snap connector 120 squeezes against the side 153 of the male snap connector 150. The elasticity of the base material of the female snap connector 120 and the size of the socket 122, which is dimensioned to be smaller in a resting state than the size of the stud, guarantees that stud is held in place. The socket 122 may be covered by a protective material, particularly electrically insulating material, such as fabric. Indeed, either or both sides of the body of the electrode may be covered. When covering the socket 122 or the opening 126, depending from the direction of insertion, a free space is preferably provided for the bottom 153 of the stud so as to prevent a force being applied to the bottom 153 by the cover to pop the stud out of the socket 122. In the case of FIG. 6, for example, the bottom 153 would be covered, i.e. non visible. The protective material would prevent the stud from coming into contact with the user's skin so as to maintain integrity of the electrode signal. Also the space between the flange 151 and the female snap connector 120 may be covered.

The female snap connector 120 has a conductive pathway 140 between the electrode 130 and the female snap connector 120 for transmitting the bio signal detected by the electrode to the telemetric device through the interface between the pinch 128 and the stud 153-155. The conductive pathway 140 is depicted in FIG. 4 and may be provided by several different methods. According to one embodiment the body 110 is made from a conductive elastomer and connected to the conductive female snap connector 120 and electrode 130 during a single stage manufacturing method by producing the three major components 110, 120, 130 in a single mold or by inserting one or more of the three major components 110, 120, 130 in the mold during molding of the body 110. According to another embodiment, the body 110 has an electrically non-conductive base material which is layered with a conductive layer, such as a printed layer of conductive ink, on either or both sides of the body 110. The conductive layer of the body 110 or the conductive body 110 itself may be bonded with the conductive female snap connector 120 and electrode 130 by ultrasonic welding, heat heading, high frequency welding, gluing with conductive adhesive, or thermal bonding, for example. Regardless of the method of providing the body 110 with electrically conductive properties it is preferable that the body 110 is bonded to the female snap connector 120 and electrode 130 in a non-detachable way, whereby it cannot be detached from the female snap connector 120 or electrode 130 without breaking the structure. Accordingly, the conductive pathway 140 is permanently formed between the female snap connector 120 and the electrode 130 without compromising points of discontinuity.

The use of the electrode unit 100 is straight-forward. Let us take a heart rate monitor belt as an exemplary application. An exemplary heart rate monitor belt has two such electrode assemblies 100 integrated to a flexible base material, such as elastic fabric, by sewing or gluing, for example. The electrode assemblies 100 are positioned adjacent in respect to each other so as to position the electrodes correctly to detect the relevant bio signals from the user's anatomy and to position the female snap connectors 120 at a correct distance from one another to correspond to the distance between the respective studs on the male snap connector of the telemetric device. Before or after putting the heart rate monitor belt or other host wearable device or garment on, the telemetric device is connected to the host wearable device or garment. The physical and electrical connection is formed at once by inserting the male snap connectors into the sockets 122 of the receiving female snap connectors 120. The insertion is facilitated by the elasticity of the elastomer of the socket 122 and optionally by the elasticity inducing relieves on the female snap connector 120. With the male snap connectors connected to the female snap connectors 120, a conductive pathway 140 is formed between the telemetric device and the electrode 130. The snug fit and positive engagement between mutually complementary shape of the male snap connectors and the female snap connectors 120 ensures a reliable mechanical connection between the telemetric device and the host wearable device or garment.

Disconnection of the telemetric device from the host wearable device or garment is equally simple. The electric and mechanical connection is broken by simply pulling the telemetric device away from the host wearable device or garment, whereby the elasticity of the female snap connector 120 facilitates yield of the socket 122 so as to release the male snap connectors from the respective female snap connectors 120. As soon as the male snap connectors become detached from the pinches 128, the electrical connection between the telemetric device and the electrode 130 is broken.

Figure 7:
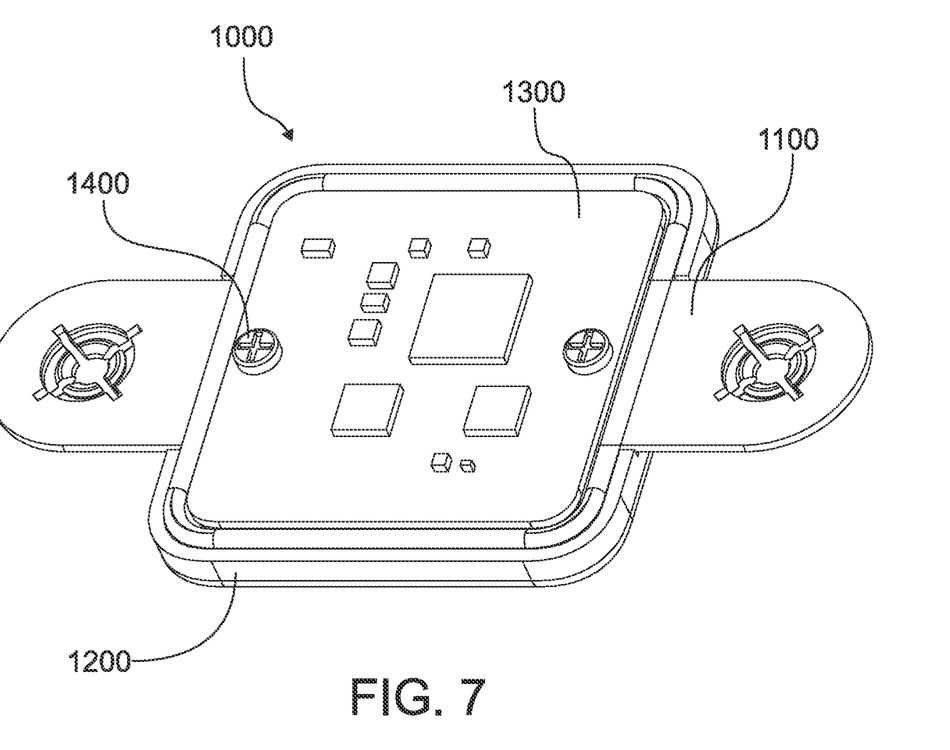
FIG. 7 illustrates a perspective view of a telemetric device in accordance with at least some embodiments of the present invention.
Figure 8:
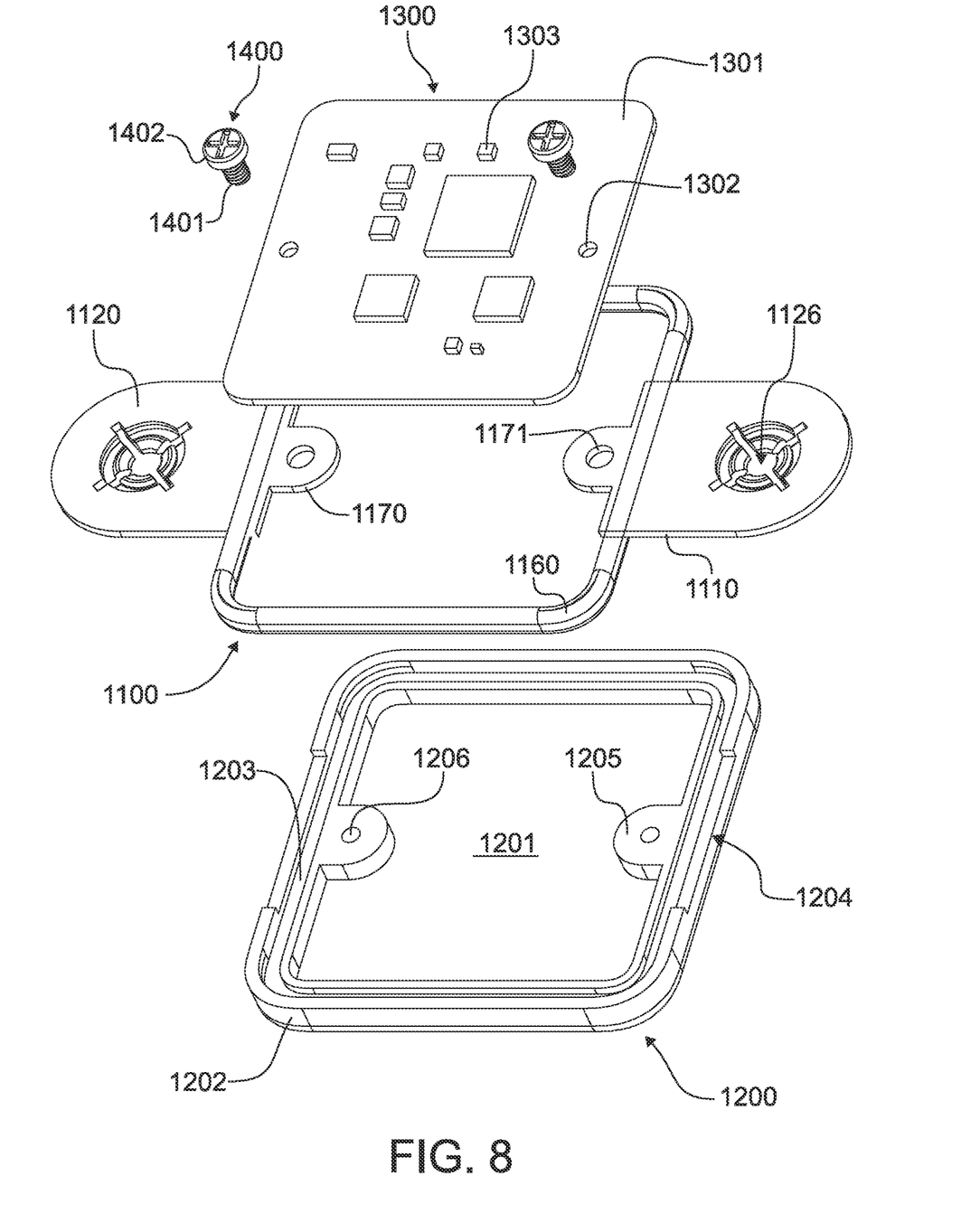
FIG. 8 illustrates a perspective exploded view of the telemetric device of FIG. 7.
Figure 9:
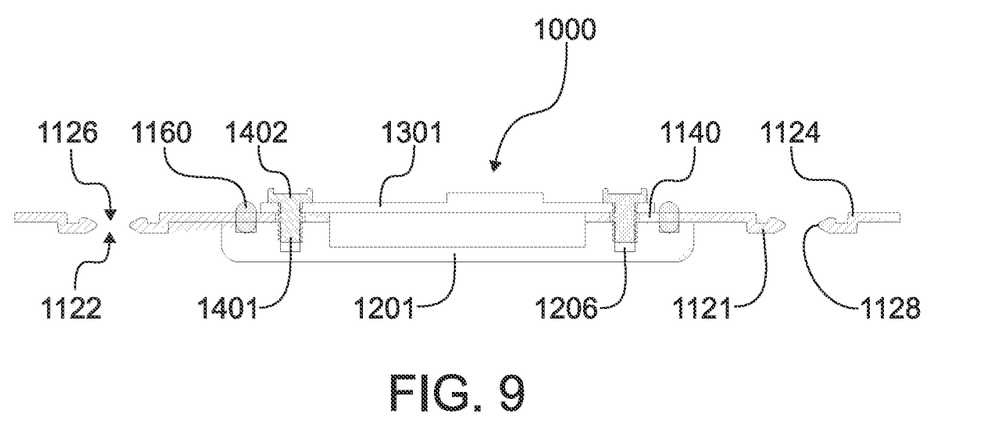
FIG. 9 illustrates a cross-sectional view of the telemetric device of FIG. 7 in an assembled configuration.

FIGS. 7 to 9 show the above-described female snap connector 120 incorporated into a telemetric device 1000, which may be a telemetric transmitter, receiver, or a transceiver, for example. A practical application of such a telemetric device 1000 could be an electronics module connected to a standard electrode equipped with a male snap connector (not shown in the FIGURES). The electronics module may include circuitry to send or to receive or both to send and receive signals relating to the bio signals being measured. Additionally or alternatively the telemetric device 1000 may include a processing core to process the bio signals received from the electrode through the electro-mechanical interface provided for by the female snap connector 120. In the following the features of the female snap connector described above are applicable to the female snap connector described here after by including a leading "1" to the applicable reference numeral.

FIG. 7 shows the exemplary telemetric device 1000 in assembled form. The telemetric device 1000 may be divided into four major components: an electro-mechanical interface 1100, an enclosure 1200, a circuit board 1300, and affixers 1400. The enclosure 1200 may include a lid but it has been omitted from FIGS. 7 to 9 for the sake of clarity.

FIG. 8 shows the telemetric device 1000 in an exploded view. The enclosure 1200 includes a cover 1201 which has been designed to exhibit a generally quadrilateral flat shape with rounded corners. Naturally, also other shapes, such as circular, oval, hexagonal, and other shapes could be equally foreseeable. The cover 1201 is surrounded by an elevated rim 1202 which protrudes from the cover 1201. The face of the rim 1202 is provided with a groove 1203 for receiving a sealing member 1160. As will transpire here after, the sealing member 1160 has been incorporated to the electro-mechanical interface 1100. The cover 1201 and the rim 1202 elevated therefrom define an inner space for receiving the internals of the telemetric device 1000. The enclosure further includes two lugs 1205 that protrude from the rim 1202 into the inner space. The purpose of the lugs 1205 is to provide mounting points for the affixers 1400. According to the illustrated embodiment, the affixers 1400 are screws with a head 1402 and a threaded shaft 1401. Accordingly, the lugs 1205 include holes 1206, preferably threaded holes, for receiving therein the threaded shafts 1401 of the affixers 1400. The lid omitted from the FIGURES may be a similar enclosure piece as shown but equipped with through holes for receiving the affixers 1400. The lid may include a similar grooved rim to seal against the electro-mechanical interface 1100. The enclosure 1100 further includes an opening 1204 made into the rim 1202 for allowing the female snap connectors 1120 to protrude out from the enclosure 1100.

FIGS. 8 and 9 show the construction of the exemplary electro-mechanical interface 1100 in detail. Generally speaking, the electro-mechanical interface 1110 includes two major components: a female snap connector 1120 for connecting to an external device, such as an electrode with a male snap connector (not shown in the FIGURES), and an associated sealing member 1160 for connecting to the enclosure 1200. The electro mechanical interface may, however, include more than one female snap connector 1120. As shown in FIGS. 7 to 9, there may be two female snap connectors 1120 sharing the sealing member 1160. More than two female snap connectors 1120 are also foreseeable.

Let us first study the female snap connectors 1120. As concerns the socket 1122 and the surrounding base 1124 and the conductive path 1140, the female snap connectors 1120 are similar to those disclosed in FIGS. 1 to 6. Compared to the female snap connectors 1120 disclosed in connection with the electrode embodiment, the female snap connectors 1120 lack the electrode and have a revised body which extends from the socket 1122 and terminates to a lug 1170. Similarly to that of the enclosure 1200, the lug 1170 of the female snap connector 1120 includes a hole 1171 which aligns with the hole 1206 of the lug 1205 of the enclosure 1200, when the telemetric device 1000 is assembled. The sealing member 1160 is designed to correspond to the shape and size of the groove 1206 on the enclosure 1200 for protecting the inner space of the telemetric device 1000 from the ambient. The sealing member 1160 is preferably constructed from a compliant material intended for sealing electrical apparatuses. Suitable materials include natural rubber, thermoplastic polyurethane (TPU), thermoplastic elastomer (TPE), silicone, particularly polydimethylsiloxane (PDMS), EPDM rubber, and styrene-butadiene rubber (SBR). The sealing member 1160 provides for a watertight seal of the enclosure, i.e. a watertight seal between the enclosure parts (bottom part and lid part). Water-tightness is particularly useful for the intended purpose of the telemetric device 1000, i.e. consumer use which may take place outdoors or even under water, e.g. during diving.

The electro-mechanical interface 1100 may be manufactured by overmolding, i.e. using the separately injection-molded or otherwise produced female snap connectors 1120 in the mold used to produce the electro-mechanical interface 1100. During injection-molding the compliant material of the sealing member 1160 encapsulates the female snap connectors 1120. Alternative manufacturing methods include gluing, laminating, ultrasonic welding, heat heading, high frequency welding, and thermal bonding. It is advantageous that the sealing member 1160 surrounds the body 1110 of the female snap connectors 1120 from both sides to safeguard proper sealing of the enclosure parts. When the electro-mechanical interface 1100 is installed into the enclosure 1200, the female snap connectors 1120 extend from the sealing member 1160 and out from the enclosure 1200 through the openings 1204 made to the rim 1202. Accordingly, the electro-mechanical interface 1100 connects the circuit board 1300 inside the enclosure 1200 to the external device outside the enclosure 1200.

The circuit board 1300 is shown in FIG. 8 to reside on the electro-mechanical interface 1100 on a side that opposes the enclosure 1200. In other words, the circuit board 1300 faces the lid. Naturally, the assembly order could be reversed by placing the circuit board 1300 between the electro-mechanical interface 1100 and the enclosure 1200. As may be seen, the circuit board 1300 has a conventional substrate 1301 with surface-mounted components 1303. Holes 1302 aligning with the holes 1206 of the lugs 1205 of the enclosure 1200 have been provided to the substrate 1301 for receiving the affixers 1400. The circuit board 1300 also has a conductive member provided on either or both sides of the circuit board around the holes 1206 for establishing an electrical connection to the female snap connector 1120.

FIG. 9 shows the advantageousness of the construction of the telemetric device 1000. The conductive and elastic nature of the female snap connector 1120 means that the male snap connector is connected to the circuit board 1301 physically and electrically with a simple piece forming two modes of connection. A physical connection between the circuit board 1301 and the male snap connector is established through the socket 1122, body 1110, and the affixer 1400. An electrical connection between the circuit board 1301 and the male snap connector is established through the pinch 1128, conductive path 1140 provided by the electrically conductive body 1110, and the electrically conductive member on the circuit board 1300 optionally aided by the electrically conductive affixer 1400, namely by the head 1402 thereof.

The telemetric device 1000 shown in connection with FIGS. 7 to 9 could also be varied. The enclosure 1200, for example, could be closed by ultrasonic welding of the enclosure parts to one another. Alternatively, the enclosure parts could be glued to each other. The lid may be omitted from the construction leaving the circuit board 1300 exposed or between the electro-mechanical interface 1100 and the enclosure 1200. Alternatively, the at least one female snap connector 1120 may be incorporated into the lid or enclosure. The incorporation may be constructed by means of overmolding, by example. The female snap connector may protrude from the enclosure or be provided on a side thereof. The cap of the female snap connector may protrude from the female snap connector or it may be embedded into the host construction, e.g. the enclosure or lid. The telemetric device 1000 may include additional structures, such as films, fabrics, etc., for making the telemetric device 1000 more concealed or integrated to the host device, such as a wearable item or garment.

Finally, additional explicit disclosures of certain embodiments are as clauses.

Clause 1: A female snap connector (120) comprising a base (124); a cap (121) opposing the base (124) for forming a depth for the snap connector (120), and a socket (122) formed into the cap (121) for receiving the stud of a co-operational male snap connector, which socket (122) is configured to undergo elastic deformation so as to comply to the passage of the complementary shape of the stud within the socket (122) during insertion and removal of the stud in the depth dimension of the female snap connector (120), wherein the base material of the female snap connector (120) is or comprises a conductive polymer.

Clause 2: The female snap connector (120) according to clause 1, wherein the base (124) and cap (121) are formed as an integral component.

Clause 3: The female snap connector (120) according to clause 1 or 2, wherein the conductive polymer is a conductive elastomer.

Clause 4: The female snap connector (120) according to any one of the preceding clauses, wherein the matrix of the conductive elastomer is selected from a list comprising:
natural rubber,
thermoplastic polyurethane (TPU),
thermoplastic elastomer (TPE),
silicone, particularly polydimethylsiloxane (PDMS),
EPDM rubber, and
styrene-butadiene rubber (SBR).

Clause 5: The female snap connector (120) according to any one of the preceding clauses, wherein the material of the conductive particles is selected from a list comprising:
carbon;
poly(3,4-ethylenedioxythiophene) polystyrene sulfonate (PEDOT:PSS);
silver;
metals;
carbon black,
graphite,
graphene,
carbon nano particles,
polyacetylene (PA),
polyaniline (PANI),
polypyrrole (PPY),
poly(3,4-ethylenedioxythiophene):poly(styrene sulfonic acid) (PEDOT:PSS), nanoparticles of silver, gold, copper, nickel, and
alloys of any of the above.

Clause 6: The female snap connector (120) according to any one of the preceding clauses, wherein the cap (121) is divided into several parts by one or more gap(s) (123) between the parts for increasing the elasticity of the cap (121).

Clause 7: The female snap connector (120) according to any one of the preceding clauses, wherein: the female snap connector (120) comprises an external side (113) for interaction with the male snap connector and an internal side (114) opposing the external side (113), and wherein the socket (122) comprises a relieved, such as bevelled, entrance surface (129) provided to the cap (121) on the external side (113), a pinch (128) connected to the entrance surface (129), and an opening (126), the narrowest part of which being defined by the pinch (128).

Clause 8: The female snap connector (120) according to clause 7, wherein the socket (122) comprises a rim (127) on the internal side (114) surrounding the opening (126) and wherein the female snap connector (120) comprises a peripheral recess (125) between the rim (127) and the surrounding base (124) for increasing the flexibility of the socket (122).

Clause 9: An electrode unit (100) comprising an electrode (130); a female snap connector (120); a body (110) mechanically connecting the electrode (130) to the female snap connector (120), and a conductive passageway (140) formed to the body (110) for electrically connecting the electrode (130) to the female snap connector (120), wherein the female snap connector (120) is one according to any one of the preceding clauses.

Clause 10: A telemetric device (1000) comprising an enclosure (1200) and a circuit board (1300) contained in the enclosure (1200), and a female snap connector (1120) according to any one of the preceding clauses 1 to 8 mechanically and electrically connected to the circuit board (1300) and extending through the enclosure (1200).

Clause 11: The telemetric device (1000) according to clause 10, wherein the enclosure (1200) comprises two cooperative enclosure parts and wherein the telemetric device (1000) comprises an electro-mechanical interface (1100) including one or more of said female snap connectors (1120) and a sealing member (1160) incorporating the one or more of said female snap connectors (1120), which sealing member (1160) seals the enclosure parts to each other.

Clause 12: The telemetric device (1000) according to clause 10 or 11, wherein the sealing member (1160) is configured to produce a watertight seal between the enclosure parts of the enclosure (1200).

Clause 13: A wearable device comprising a host garment configured to be worn by a user, a first electrode unit (100) according to clause 9 incorporated to the host garment, and a second electrode unit (100) according to clause 9 incorporated to the host garment and positioned such that the female snap connectors (120) are set adjacent to each other so as to receive cooperative male snap connectors of an associated telemetric device.

Clause 14: The wearable device according to clause 13, wherein the wearable device comprises a telemetric device comprising cooperative male snap connectors connected to the host garment through the female snap connectors of the first and second electrode assemblies.

Clause 15: A method for manufacturing a female snap connector (120) according to any one of the preceding clauses 1 to 8, comprising producing the base (124) and cap (121) with an additive manufacturing method into an integral component.

Clause 16: A method for manufacturing an electrode unit (100) according to clause 9, comprising providing the electrode (130) and the body (110), producing the female snap connector (120) with the method according to clause 14, and providing the conductive passageway (140) between the female snap connector (120) and the electrode (130) by bonding the body (110), the female snap connector (120), and electrode (130) together as an integral component, wherein the conductive passageway (140) is formed at least partly by the body (110) comprising an electrically conductive base material connecting the snap connector (120) to the electrode (130) or by the body (110) comprising an electrically conductive layer connecting the snap connector (120) to the electrode (130).

Clause 17: The method according to clause 16, wherein said bonding comprises casting, ultrasonic welding, heat heading, high frequency welding, gluing with conductive adhesive, or thermal bonding of the female snap connector (120), and electrode (130) together as an integral component.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", i.e. a singular form, throughout this document does not exclude a plurality.

| REFERENCE SIGNS LIST | |
|---|---|
| No. | Feature |
| 100 | electrode unit |
| 110 | body |
| 111 | snap end |
| 112 | electrode end |
| 113 | external side |
| 114 | internal side |
| 120 | female snap connector |
| 121 | cap |
| 122 | socket |
| 123 | slit |
| 124 | base |
| 125 | peripheral recess |
| 126 | opening |
| 127 | rim |

REFERENCE SIGNS LIST

| No. | Feature |
|---|---|
| 128 | pinch |
| 129a | entrance surface |
| 129b | rear surface |
| 130 | electrode |
| 140 | conductive path |
| 150 | male snap connector |
| 151 | flange |
| 152 | side |
| 153 | bottom |
| 154 | transition |
| 155 | transition |
| 1000 | telemetric device, e.g. telemetric transceiver |
| 1100 | electro-mechanical interface |
| 1110 | body |
| 1120 | female snap connector |
| 1121 | cap |
| 1122 | socket |
| 1124 | base |
| 1126 | opening |
| 1140 | conductive path |
| 1160 | sealing member |
| 1170 | lug |
| 1171 | hole |
| 1200 | enclosure |
| 1201 | cover |
| 1202 | rim |
| 1203 | groove |
| 1204 | opening |
| 1205 | lug |
| 1206 | hole |
| 1300 | circuit board |
| 1301 | substrate |
| 1302 | hole |
| 1303 | component |
| 1400 | affixer |
| 1401 | shaft |
| 1402 | head |

The invention claimed is:

1. A female snap connector comprising:
a base;
a cap opposing the base for forming a depth for the female snap connector, and
a socket formed into the cap for receiving a stud of a co-operational male snap connector, which socket is configured to undergo elastic deformation so as to comply to the passage of the complementary shape of the stud within the socket during insertion and removal of the stud in the depth dimension of the female snap connector,
an external side for interaction with the male snap connector, and
an internal side opposing the external side,
wherein base material of the female snap connector is or comprises a conductive elastomer,
wherein the socket comprises: a relieved entrance surface provided to the cap on the external side, a pinch connected to the entrance surface, an opening, the narrowest part of which being defined by the pinch, and a rim on the internal side surrounding the opening, and the female snap connector comprises a peripheral recess between the rim and the base for increasing the flexibility of the socket.

2. The female snap connector according to claim 1, wherein the base and the cap are formed as an integral component.

3. The female snap connector according to claim 1, wherein a matrix of the conductive elastomer is selected from the group consisting of natural rubber, thermoplastic polyurethane (TPU), thermoplastic elastomer (TPE), silicone, particularly polydimethylsiloxane (PDMS), EPDM rubber, and styrene-butadiene rubber (SBR).

4. The female snap connector according to claim 1, wherein the base material comprises conductive particles, wherein the material of the conductive particles is selected from the group consisting of carbon; poly(3,4-ethylenedioxythiophene) polystyrene sulfonate (PEDOT:PSS), silver, metals, carbon black, graphite, graphene, carbon nano particles, polyacetylene (PA), polyaniline (PANI), polypyrrole (PPY), poly(3,4-ethylenedioxythiophene):poly(styrene sulfonic acid) (PEDOT:PSS), nanoparticles of silver, gold, copper, nickel, and alloys of any of the above.

5. The female snap connector according to claim 1, wherein the cap is divided into several parts by one or more gap(s) between the parts for increasing the elasticity of the cap.

6. An electrode unit comprising: an electrode; a female snap connector; a body mechanically connecting the electrode to the female snap connector, and a conductive passageway formed to the body for electrically connecting the electrode to the female snap connector, wherein the female snap connector is one according to claim 1.

7. A telemetric device comprising:
an enclosure, and a circuit board contained in the enclosure,
further comprising a female snap connector according to claim 1 mechanically and electrically connected to the circuit board and extending through the enclosure.

8. The telemetric device according to claim 7, wherein: the enclosure comprises two cooperative enclosure parts, and wherein the telemetric device comprises an electro-mechanical interface including one or more of said female snap connectors and a sealing member incorporating the one or more of said female snap connectors, which sealing member seals the enclosure parts to each other.

9. The telemetric device according to claim 7, wherein the sealing member is configured to produce a watertight seal between the enclosure parts of the enclosure.

10. A wearable device comprising: a host garment configured to be worn by a user; a first electrode unit according to claim 6 incorporated to the host garment, and a second electrode unit according to claim 6 incorporated to the host garment and positioned such that the female snap connectors are set adjacent to each other so as to receive cooperative male snap connectors of an associated telemetric device.

11. The wearable device according to claim 10, wherein the wearable device comprises a telemetric device comprising cooperative male snap connectors connected to the host garment through the female snap connectors of the first and second electrode assemblies.

12. A method for manufacturing a female snap connector according to claim 1, further comprising producing the base and the cap with an additive manufacturing method into an integral component.

13. A method for manufacturing an electrode unit, which comprises: an electrode; a female snap connector; a body mechanically connecting the electrode to the female snap connector, and a conductive passageway formed to the body for electrically connecting the electrode to the female snap connector, which female snap connector comprises: a base; a cap opposing the base for forming a depth for the female snap connector, and a socket formed into the cap for receiving a stud of a co-operational male snap connector, which socket is configured to undergo elastic deformation so as to comply to the passage of the complementary shape of the stud within the socket during insertion and removal of the stud in the depth dimension of the female snap connector, which socket comprises:

a relieved entrance surface provided to the cap on the external side, a pinch connected to the entrance surface, an opening, the narrowest part of which being defined by the pinch, and a rim on the internal side surrounding the opening, an external side for interaction with the male snap connector, an internal side opposing the external side, a peripheral recess between the rim and the base for increasing the flexibility of the socket, wherein base material of the female snap connector is or comprises a conductive elastomer, wherein the method comprises: providing the electrode and the body; producing the female snap connector with a method, in which the base and the cap are produced with an additive manufacturing method into an integral component, and in providing the conductive passageway between the female snap connector and the electrode by bonding the body, the female snap connector, and the electrode together as an integral component, wherein the conductive passageway is formed at least partly by:

the body comprising an electrically conductive base material connecting the snap connector to the electrode, or by the body comprising an electrically conductive layer connecting the snap connector to the electrode.

14. The method according to claim 13, wherein said bonding comprises casting, ultrasonic welding, heat heading, high frequency welding, gluing with conductive adhesive, or thermal bonding of the female snap connector and the electrode together as an integral component.

* * * * *